United States Patent [19]

Abend et al.

[11] 4,282,577

[45] Aug. 4, 1981

[54] PROCESS AND APPARATUS FOR AUTOMATICALLY ADJUSTING ULTRASONIC TEST HEADS

[76] Inventors: Klaus Abend, AM Kirschberg 1, 6470 Budingen; Raimund Lang, Friedensstrasse 29, 8755 Wasserlos, both of Fed. Rep. of Germany

[21] Appl. No.: 52,786

[22] Filed: Jun. 28, 1979

[30] Foreign Application Priority Data

Jun. 28, 1978 [DE] Fed. Rep. of Germany ....... 2828273

[51] Int. Cl.³ .................... G01N 29/04; G06F 15/46
[52] U.S. Cl. .................... 364/507; 364/559; 73/634
[58] Field of Search ............ 364/507, 559, 571, 550; 73/1 E, 622, 801, 634, 635; 250/358 P

[56] References Cited

U.S. PATENT DOCUMENTS

| 3,531,977 | 10/1970 | Chaskelis et al. | 73/1 R |
|---|---|---|---|
| 3,864,660 | 2/1975 | Ranalli et al. | 73/622 X |
| 3,898,838 | 8/1975 | Connelly | 73/634 |
| 3,924,444 | 12/1975 | Heyman et al. | 73/1 R |
| 3,933,026 | 1/1976 | Ham et al. | 73/1 R |
| 3,969,926 | 7/1976 | Wlaker et al. | 73/634 X |
| 3,981,184 | 9/1976 | Matay | 73/622 X |
| 4,062,237 | 12/1977 | Fox | 364/416 X |
| 4,064,735 | 12/1977 | Hutchison et al. | 73/1 R |
| 4,109,642 | 8/1978 | Reid et al. | 73/622 X |

Primary Examiner—Edward J. Wise
Attorney, Agent, or Firm—Cushman, Darby & Cushman

[57] ABSTRACT

There is described a process for automatically adjusting the angle of inclination and the focus distance of ultrasonic heads in reference to the test piece in devices for the non-destructive testing of work pieces, especially tubes, using a computer where both the adjustment of the angle and the distance are adjusted and examined in each case by two angular transmitters operating mechanically independent from one another and absolutely coded for use by program of the computer. There is also described an apparatus for carrying out the process.

5 Claims, 2 Drawing Figures

PROCESS AND APPARATUS FOR AUTOMATICALLY ADJUSTING ULTRASONIC TEST HEADS

BACKGROUND OF THE INVENTION

The invention is directed to a process and apparatus for automatically adjusting the testing position of an ultrasonic testing head in reference to the test piece in devices for testing work pieces without destruction, especially tubes, using a computer.

It is known that with a change in dimensions of test pieces, e.g. tubes, the ultrasonic head must be adjusted anew. In this connection important parameters of adjustment are, among others, the distance of the testing (examination) head to the object measured bearing in mind the testing head characteristics as well as the inclination of the testing head to the object being measured.

The adjustment of these parameters takes place manually, also partially by use of mechanical assisting devices. Thereby the operator is compelled to establish a most optimal possible test head piece substantially by tests. This is time consuming, requires experience and skill and above all in regard to reproducible adjustments with interim adjustment of the apparatus frequently proceeds very problematically. The manual adjustment takes place in such manner that, e.g. with tubes, inner and outer surface errors are evaluated with equal sensitivity in an echo evaluation unit. The evaluation of indications of error above all with the test head adjustment is undertaken based on an amplitude-transmission time-representation, normally on an oscillogram screen.

There have been attempts to reduce these expenses of change over and control times, to improve the reproductivity of the test results and to make the adjusting operation as independent as possible from service personnel. This is reported for example in the periodical "Material prüfung", vol. 20 (1978), No. 4, pages 143-146, furthermore in the German Offenlegungsschrifts Nos. 2636401; 2632674 and 2632680. For this purpose the necessary electronic tests and evaluation programs are controlled by means of a computer. The decisive disadvantages described initially, the manual adjustments of the mechanics, however, remains.

Therefore it was the problem of the present invention to provide a process and apparatus for automatically adjusting the angle of inclination in the focus distance supersonic test heads in reference to the test piece in apparatus for testing work pieces, especially tubes, without destruction, using a computer, which avoids the above mentioned disadvantages and especially makes unnecessary a manual subsequent adjustment of the test head.

SUMMARY OF THE INVENTION

This problem was solved by the invention by adjusting and examining both the angle and the distance by two angle transmitters (or givers) operating mechanically independently from one another and absolutely coded for use by program of the computer.

BRIEF DESCRIPTION OF THE DRAWINGS

In the drawings like numerals refer to like parts.

DESCRIPTION OF THE PREFFERED EMBODIMENTS

Figure 1:
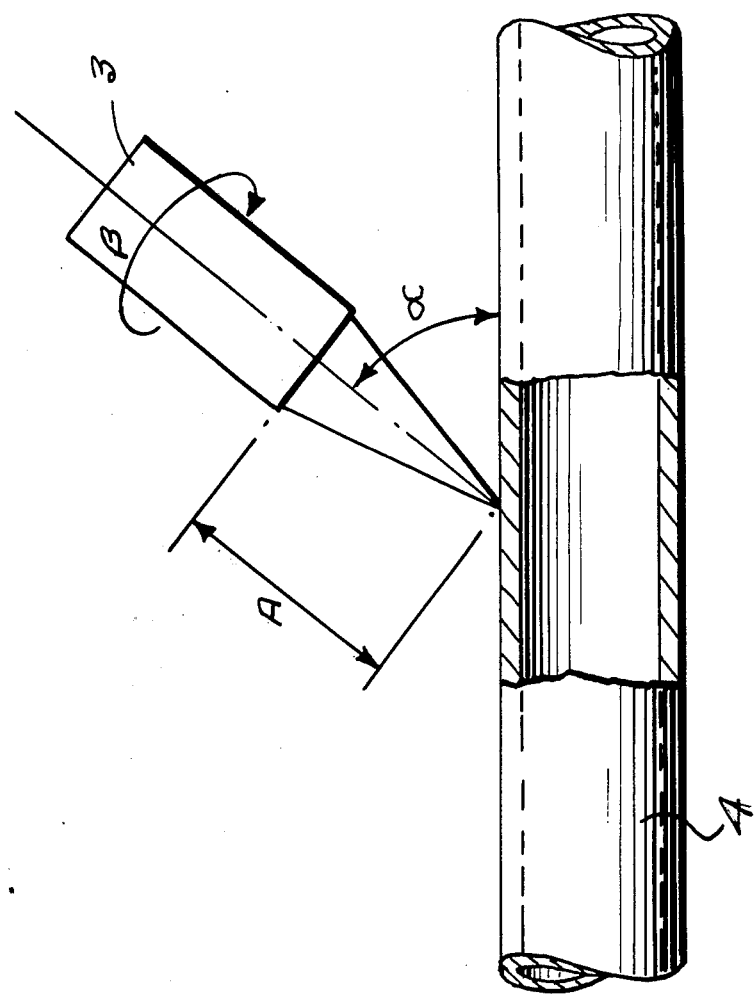
FIG. 1 schematically shows the adjusting parameter of the process of the invention.

Referring more specifically to FIG. 1 of the drawings the inclination ($\alpha$) of the test head 3 to the test piece 4, its distance (A) to the test piece 4 as well as the orientation ($\beta$) of the line of focus of the test head 3 (in the case of line focus) to the test piece are adjusted independent of each other by way of a mechanical device, mechanically independent from the other conduits of the other adjustment parameters via an for instant absolutely coded angle computer. In place of the transmitter there can also be used other motion pickups. The control of the adjustment of each parameter takes place through a computer via a second for instant absolutely coded angular pickup, which independent of the adjustment conduit takes up the true position of the test head per parameter.

Figure 2:
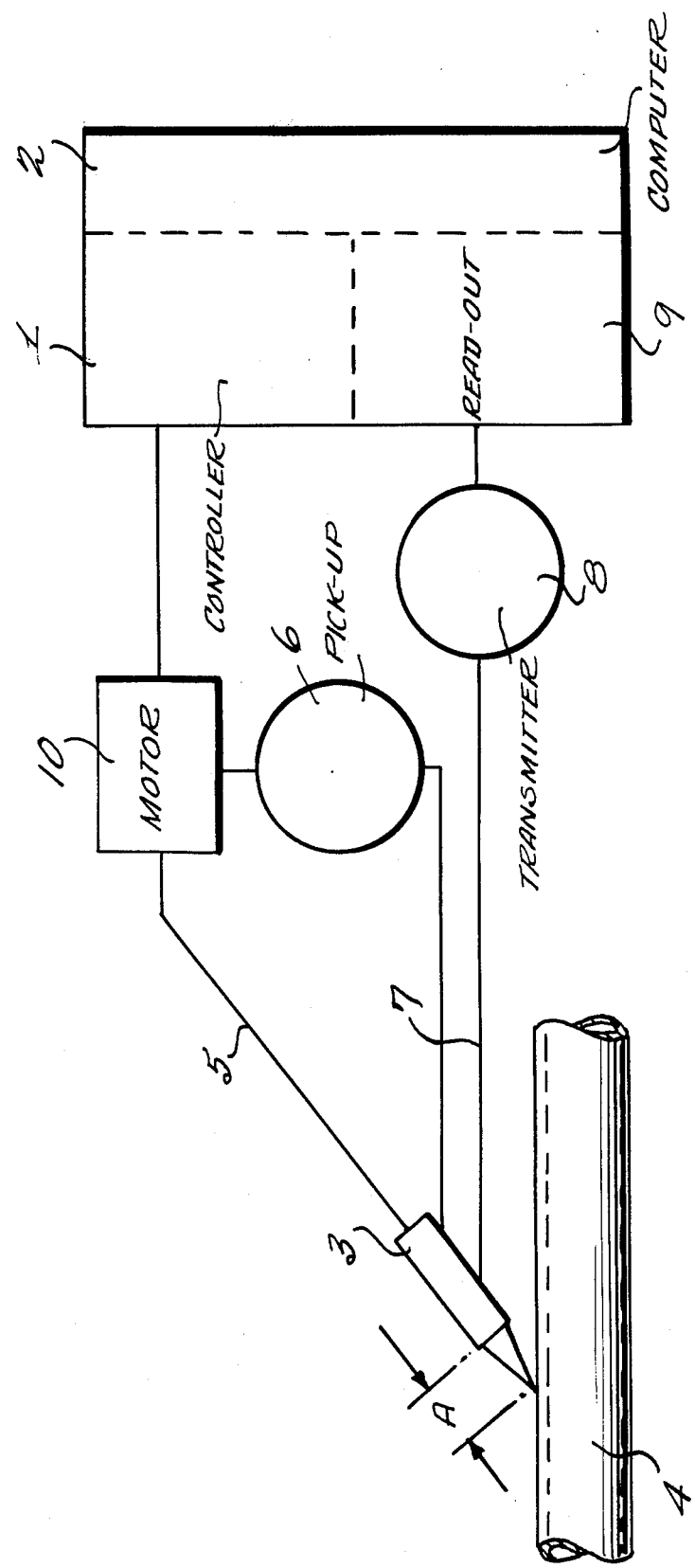
FIG. 2 schematically illustrates a preferred apparatus for carrying out this process.

Referring to FIG. 2 the distance A of the test head 3 to the surface of the tube 4 is controlled from the controller 1 and/or computer 2 via a step motor 10. The control signals are given out of the absolutely coded angular transmitter or other motion pickup 6 connected to the control conduit 5 for the information of the position of the test head 3. There is installed independent from the control conduit 5 a measuring conduit 7 which controls the actual position (distance A) in the readout device 9 via a further absolutely coded angular transmitter 8 and/or with a computer 2 connected to it and prudently issues new commands for the control conduit 5. Thus it is guaranteed that the above calculated distance A also is actually attained through independent subsequent measurement.

For the adjustment of the inclination ($\alpha$) of the test head as well as for focus line test 3 of its orientation ($\beta$) the control conduit 5 is correspondingly equivalently used with angular transmitter 6 and the measuring conduit 7 with angular transmitter 8.

With the process of the invention and the apparatus of the invention it is possible:

1. to carry out a remote controlled absolute adjustment of the test heads;
2. to automatically undertake by above programs changes of dimensions of test pieces and therewith needed adjustments in the test heads.

The reproducibility of test pieces is improved considerably, the change over times reduced substantially and the regulation of the test head as well as the test piece made objectively and consequently made independent of service personnel.

The entire disclosure of German priority application No. P 28 28 273.7 is hereby incorporated by reference.

What is claimed is:

1. An apparatus for regulating the angle of inclination and the focus distance of an ultrasonic test head in relation to a test piece of a device for the non-destructive testing of a work piece comprising in combination:
   a test head;
   a computer for executing a test program, said computer providing an instruction signal for controlling the angle of inclination and focus distance of the head;
   a step motor coupled to said computer and adapted to receive an instruction signal therefrom,
   a first absolutely coded angular transmitter connected to the test head via the stepping motor for indicating the actual position of the test head, and a second absolutely coded angular transmitter, mechanically independent from the first angular transmitter, for controlling the position of the test head.

2. An apparatus according to claim 1 further including
a control circuit coupled between the step motor and the test head, and a measuring conduit independent of said control circuit, coupled between the second angular transmitter and the test head.

3. Apparatus for adjusting the angle of inclination and focus distance of an ultrasonic test head in relation to a test piece comprising:
computer means for executing a test program and issuing instruction signals indicating desired angles of inclination and desired focus distances of the test head for various tests;
position control means, responsive to the instruction signals, for adjusting the angle of inclination and focus distance of the test head;
measuring means, independent of the position control means, for measuring the angle of inclination and focus distance of the test head;
transmitters, coupled to said measuring means, for generating absolutely coded signals indicative of values measured by the measuring means; and
means for coupling the coded signals to the computer means, the computer means (a) comparing the coded signals with data representing a desired angle of inclination and focus distance and (b) adjusting an instruction signal to correct an actual angle of inclination and/or focus distance, as measured, to the desired angle of inclination and focus distance.

4. Apparatus according to claim 3 wherein the test piece is a tube.

5. A method for adjusting the angle of inclination and focus distance of an ultrasonic test head in relation to a test piece comprising:
generating, by computer means executing a test program, instruction signals indicating desired angles of inclination and desired focus distances for various tests;
adjusting by means responsive to the instruction signals, the angle of inclination and focus distance of the test head;
independently measuring the angle of inclination and focus distance of the test head;
generating an absolutely coded signal indicative of the values measured; and
comparing the coded signals with data representing a desired angle of inclination and focus distance and adjusting an instruction signal to the desired angle of inclination and focus distance.

* * * * *